(12) United States Patent
Ye et al.

(10) Patent No.: US 8,937,076 B2
(45) Date of Patent: Jan. 20, 2015

(54) CRYSTALLINE FORM OF ENTECAVIR, ITS PREPARATION AND THE PHARMACEUTICAL COMPOSITION AND USES THEREOF

(75) Inventors: Weidong Ye, Huancheng Donglu (CN); Jianyong Yuan, Huancheng Donglu (CN); Jingjing Nie, Huancheng Donglu (CN); Duanjun Xu, Huancheng Donglu (CN); Chaotian Chen, Huancheng Donglu (CN)

(73) Assignee: Zhejiang Medicine Co., Ltd. Xinchang Pharmaceutical Factory (CN)

( * ) Notice: Subject to any disclaimer, the term of this patent is extended or adjusted under 35 U.S.C. 154(b) by 673 days.

(21) Appl. No.: 12/527,215

(22) PCT Filed: Jan. 31, 2008

(86) PCT No.: PCT/CN2008/000249
§ 371 (c)(1),
(2), (4) Date: Mar. 22, 2010

(87) PCT Pub. No.: WO2008/098471
PCT Pub. Date: Aug. 21, 2008

(65) Prior Publication Data
US 2010/0210669 A1 Aug. 19, 2010

(30) Foreign Application Priority Data
Feb. 14, 2007 (CN) .......................... 2007 1 0004988

(51) Int. Cl.
*A61K 31/522* (2006.01)
*C07D 473/18* (2006.01)

(52) U.S. Cl.
CPC .................................. *C07D 473/18* (2013.01)
USPC ..................................... 514/263.38; 544/276

(58) Field of Classification Search
CPC ..... C07D 473/18; A61K 31/522; A61K 31/52
USPC ...................................... 544/276; 514/263.37
See application file for complete search history.

(56) References Cited

U.S. PATENT DOCUMENTS

| | | | |
|---|---|---|---|
| 2,918,477 A | 12/1959 | Cattapan et al. | |
| 5,206,244 A * | 4/1993 | Zahler et al. ................ | 514/263.3 |
| 2004/0192912 A1* | 9/2004 | Pendri et al. ................... | 544/276 |
| 2005/0272932 A1* | 12/2005 | Zhou et al. ..................... | 544/276 |
| 2007/0060599 A1* | 3/2007 | DiMarco et al. .......... | 514/263.37 |
| 2010/0144828 A1 | 6/2010 | Wu et al. | |
| 2010/0311827 A1 | 12/2010 | Daneshtalab et al. | |
| 2011/0201809 A1* | 8/2011 | Hu et al. ........................ | 544/276 |

FOREIGN PATENT DOCUMENTS

| | | | |
|---|---|---|---|
| CN | 1175411 | 3/1998 | |
| CN | 1415758 | 5/2003 | |
| CN | 1657601 | 8/2005 | |
| CN | 1861602 A1 * | 11/2006 | |
| EP | 0159180 | 10/1985 | |
| EP | 0265071 | 4/1988 | |
| EP | 1200462 | 5/2005 | |
| JP | 2006 298802 | 11/2006 | |
| WO | 9809964 | 3/1998 | |
| WO | WO 0164221 A1 * | 9/2001 | ............. A61K 31/52 |
| WO | 2004052310 | 6/2004 | |
| WO | 2005118585 | 12/2005 | |
| WO | 2007030657 | 3/2007 | |
| WO | 2008098471 | 8/2008 | |
| WO | 2009046618 | 4/2009 | |

OTHER PUBLICATIONS

Translation of CN1861602A (Nov. 15, 2006).*
"Tilde." Merriam-Webster.com. Merriam-Webster, n.d. Web. Mar. 19, 2014. <http://www.merriam-webster.com/dictionary/tilde>.*
CDC, "Human Immunodeficiency Virus Type 2," Oct. 1998.
Kashman, et al., "The Calanolides, a Novel HIV-Inhibitory Class of Coumarin Derivatives from the Tropical Rainforest Tree, Calophyllum Ianigerum." J. Med. Chem. 1992;35, pp. 2735-2743.
Dittmar, et al., "HIV: Epidemiology and Strategies for Therapy and Vaccination," PubMed, Intervirology, 2002;45(4-6), pp. 260-266.
Miles, K. "The Growing HIV Pandemic," PubMed, Community Pract. Aug. 2005;78(8), pp. 292-294.
The Merck Manual, "Human Immunodeficiency Virus (HIV)," pp. 1-16, Accessed Aug. 27, 2009.
The Merck Manual, "Respiratory Viruses," pp. 1-2, Accessed Aug. 27, 2009.
Morissette, et al., "High-Throughput Crystallization: Polymorphs, Salts, co-Crystals and Solvates of Pharmaceutical Solids," Advanced Drug Delivery Reviews 2004, 56, pp. 275-300.
Souillac, et al., "Characterization of Delivery Systems, Differential Scanning Calorimetry," Encyclopedia of Controlled Drug Delivery, 1999, pp. 212-227, John Wiley & Sons.
Vippagunta, et al., "Crystalline Solids," Advanced Drug Delivery Reviews, 2001, 48, pp. 3-26.
Ma, et al., "Synthesis of Chlorogenic Acid Derivatives with Promising Antifungal Activity," Bioorganic & Medicinal Chemistry, 2007, 15, pp. 6830-6833.
The Merck Manual, "Acute Viral Hepatitis," pp. 1-8, Accessed Aug. 27, 2009.

* cited by examiner

*Primary Examiner* — Golam M M Shameem
*Assistant Examiner* — Laura Daniel
(74) *Attorney, Agent, or Firm* — William D. Hare, Esq.; McNeely, Hare & War, LLP

(57) ABSTRACT

The present invention relates to a crystalline form of entecavir and its process for preparation, and provides a pharmaceutical composition comprising a therapeutically effective amount of the crystalline form of entecavir. Furthermore, the present invention also provides a use of the crystalline form of entecavir in preparation for a medicament for the treatment of hepatitis B viral infections. The present invention is beneficial toe preparations for pharmaceutical formulations and enhancements of its bioavailability.

8 Claims, 2 Drawing Sheets

CRYSTALLINE FORM OF ENTECAVIR, ITS PREPARATION AND THE PHARMACEUTICAL COMPOSITION AND USES THEREOF

FIELD OF THE INVENTION

The present invention relates to analogues of 2'-cyclopentyl deoxyguanosine, especially relates to crystalline forms of entecavir, its preparation and the pharmaceutical composition and uses thereof.

BACKGROUND OF THE INVENTION

Entecavir (entecavir or BMS-2000475) which has inhibited effect on polymerase of hepatitis B virus (HBV) is analogues of 2 cyclopentyl deoxyguanosine. Entecavir's chemical name is referred to as [1S-(1α, 3α, 4β)]-2-amino-1,9-dihydro-9-[4-hydroxy-3-hydroxymethyl]-2-methylenecyclopentyl]-6H-purin-6-one, and its molecule structural formula has the following general formula (I):

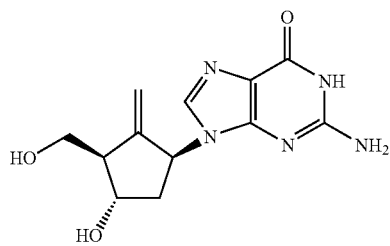

(I)

Entecavir could be converted to an active entecavir triphosphate by phosphorylation. Entecavir triphosphate could compete with triphosphate deoxyguanosine which is a natural substrate of HBV polymerase to inhibit activities of viral polymerase (reverse transcriptase). Entecavir exhibits much times stronger effects than Lamivudine in experiments such as antiviral activities, resistances, cross resistances and the like.

Many methods of preparing for entecavir compounds and a method for obtaining a little entecavir solid separated by resin column chromatography are described in U.S. Pat. No. 5,206,244 and WO98/0994. The method of preparing for non-crystalline forms of entecavir is disclosed in Chinese Patent Publication No. CN1660846A. But the crystalline forms of entecavir and its performances are not researched and reported in the above-mentioned patents.

In recent years, drug polymorphism is increasingly becoming indispensable and important constituents in the processes of drug researches and quality controls of drug production, and causes more and more people's concerns in the pharmaceutical fields. To carry out the research of drug polymorphism is helpful to bioactivity choices of new drug compounds, is helpful to enhancements of bioavailability to promote clinical effects, is helpful to choices and designs of drug administration route and determinations of technological parameters of pharmaceutical preparation to enhance quality of drug production. Different crystal forms of the same drug may have significant differences in bioavailability. Certain crystal form may have higher bioactivity than other crystal forms of the same drug.

SUMMARY OF THE INVENTION

It is an object of the present invention to provide crystalline forms of entecavir and its preparation in order to overcome deficiencies of crystalline forms of entecavir currently.

It is another object of the present invention further to provide a pharmaceutical composition comprising a therapeutically effective amount of the crystalline form of entecavir.

Furthermore, it is still another object of the present invention further to provide the use of the pharmaceutical composition comprising crystalline forms of entecavir in preparation of a medicament for the treatment of hepatitis B.

The crystalline form of entecavir of the present invention has the following general formula (I):

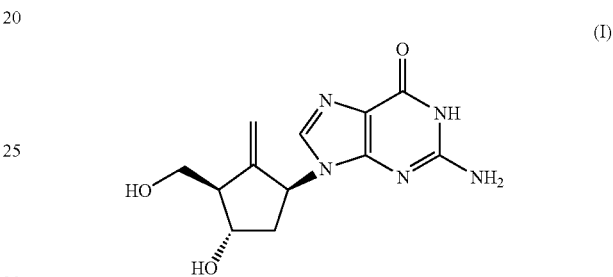

(I)

Wherein, it has the same characteristic as the X-ray powder crystal diffraction pattern of FIG. 1. And the X-ray powder crystal diffraction peaks at 2θ is 5.3±0.2°, 15.6±0.2°, and 21.2±0.2° have a strong diffraction peaks, when measured using CuKa radiation. The crystalline form of entecavir is a desolvation product or a product containing water of crystallization. Said product containing water of crystallization is the crystalline form of entecavir containing one water of crystallization.

According to the present invention, it provides a method of preparing for the crystalline form of entecavir comprising the following steps:

(1) dissolving a crude product of entecavir in a polar solvent at the temperature of 50~90° C. in the ratio of the crude product of entecavir to the polar solvent 1: 20~60 (mass) to give the entecavir solution;

(2) cooling said entecavir solution to the temperature below 50° C. and a crystal separated out of it;

(3) separating said crystal to give the crystalline form of entecavir.

Wherein, the above-mentioned cooling could be carried in a slow-speed and the crystalline form of entecavir could be obtained at the temperature of 50° C. by vacuum drying. Said polar solvent is a mixed liquid of water and mono alcohol or lower ketone, wherein the volume ratio of monohydroxy alcohol or lower ketone to water is 0~50%. Said monohydroxy alcohol is a C1-C4 monohydroxy alcohol, preferably methanol, ethanol, propanol, isopropanol, n-butanol, isobutanol. And said polar solvent preferably is water. Moreover, said lower ketone is acetone, butanone.

According to the present invention, it provides a pharmaceutical composition which comprises a therapeutically effective amount of the crystalline form of entecavir and pharmaceutically acceptable carriers; besides, the pharmaceutical composition could be any one of acceptable pharmaceutical dosage forms in pharmaceutics, preferably, it may be tablets, capsules, granules, oral solutions, injections. The therapeutically effective amount of the entecavir is 0.01~10 mg, and the optimum amount is 0.1~1 mg.

According to the present invention, it provides the use of the crystalline form of entecavir in preparation of a medicament for the treatment of hepatitis B viral infections.

The advantages of the present invention that it is beneficial for preparations of pharmaceutical formulations and enhancements of its bioavailability.

The effects of the present invention that it provides a crystalline form of entecavir and its process for preparation. The process is simple and easy to be industrialized productions.

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention. Firstly methods of preparation and analysis and structural characterization of the crystalline form of entecavir of the present invention are illustrated.

1. The Preparation for the Crystalline Form of Entecavir

A crude product of entecavir is dissolved with stirring in a polar solvent at the temperature of 50~90° C. in the ratio of the crude product of entecavir to the polar solvent 1: 20~60 (mass). The above solution is slowly cooled to the temperature below 50° C., and a flaky crystal is separated out of it. After filtration, the crystal is dried in vacuum at the temperature of 50° C. to give the crystalline form of entecavir. It is found by us that the method is easy to operate and has a good repeatability.

2. The Analysis and Characterization of the Crystalline Form of Entecavir

The crystalline form of entecavir is characterized in its structure and performance by using a detection means, such as X-ray diffraction of powder crystal, thermogravimetry-differential scanning calorimetry instrument (TG-DSC), transmission electron microscope, Fourier transform infrared spectrogram.

X-Ray Diffraction of Powder Crystal:

The sample of crystalline form of entecavir is characterized by using Bruker D8 Advance X-ray powder crystal diffraction instruction, and the range of diffraction 2θ angle is 3°~60°, a scanning step width is 0.02°, a rate is 0.2 s per step, and a X-ray wavelength λ is 0.15406 nm. For X-ray powder crystal diffraction pattern, please refer to FIG. 1.

Figure 1:
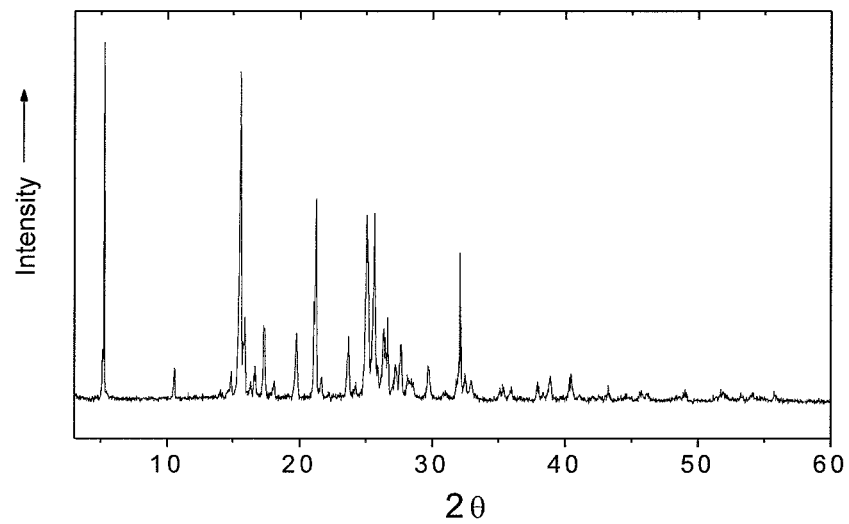
FIG. 1 is a X-ray powder crystal diffraction pattern of the crystalline form of entecavir.

FIG. 1 shows many sharp-pointed diffraction peaks, wherein there is stronger diffraction peaks when 2θ=5.282° (d=16.7171 Å), 2θ=15.560° (d=5.6902 Å), 2θ=21.236° (d=4.1803 Å). It confirms that the sample of entecavir is the crystalline form of entecavir. For the datum of the major diffraction peaks, please refer to Table 1.

TABLE 1

| 2θ (°) | d (Å) | I % |
|---|---|---|
| 5.282 | 16.7171 | 100.0 |
| 10.573 | 8.3601 | 8.6 |
| 14.876 | 5.9501 | 6.0 |
| 15.560 | 5.6902 | 89.7 |
| 15.895 | 5.5710 | 21.4 |
| 16.643 | 5.3223 | 7.3 |
| 17.304 | 5.1205 | 19.5 |
| 19.741 | 4.4935 | 18.1 |
| 21.236 | 4.1803 | 55.5 |
| 21.658 | 4.0999 | 6.1 |
| 23.681 | 3.7540 | 16.3 |
| 25.040 | 3.5533 | 49.5 |
| 25.619 | 3.4743 | 48.8 |
| 25.844 | 3.4445 | 7.6 |
| 26.338 | 3.3810 | 16.7 |
| 26.637 | 3.3438 | 20.6 |
| 27.201 | 3.2757 | 7.9 |
| 27.655 | 3.2229 | 13.5 |
| 28.143 | 3.1682 | 5.5 |
| 28.440 | 3.1358 | 4.6 |
| 29.686 | 3.0069 | 9.2 |
| 32.085 | 2.7874 | 40.0 |
| 32.466 | 2.7555 | 6.8 |
| 32.939 | 2.7170 | 5.5 |
| 38.862 | 2.3155 | 6.3 |
| 40.443 | 2.2285 | 7.1 |

In the table 1, 2θ is a diffraction angle, d is an interplanar spacing of crystal, I is a relative intensity of diffraction peak.

Figure 2:
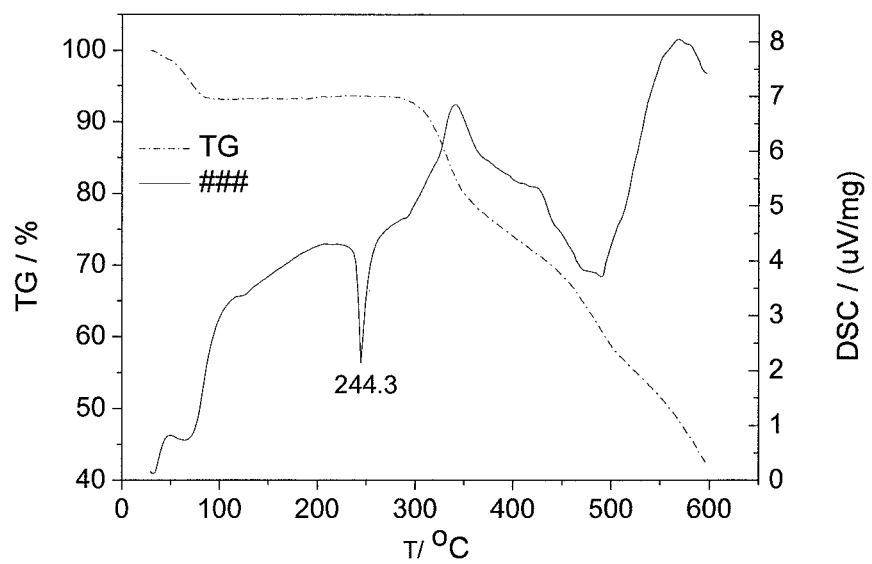
FIG. 2 is thermogravimetry-differential scanning calorimetry pattern of the crystalline form of entecavir.

Thermogravimetry-Differential Scanning Calorimetry (TG-DSC) Analysis:

Thermogravimetry-Differential Scanning calorimetry analysis pattern of the crystalline form of entecavir under $N_2$ atmosphere is measured by using NETZSCH STA 409 PG/PC type TG-DSC instrument (refer to FIG. 2). The heating rate of the sample is 20 K/min.

FIG. 2 shows that the weight loss of the sample is about 6% at temperature of 80° C., which indicates that the sample is a complex of entecavir and a crystalline water of 1:1. The attached FIG. 2 shows a sharp-pointed endothermic peak at the temperature of 244° C. without any weightlessness. It illustrates that the melting point of the sample is about 244° C. under the experimental conditions, and the sample will be decomposed when reaching the temperature of 300° C.

Figure 3:
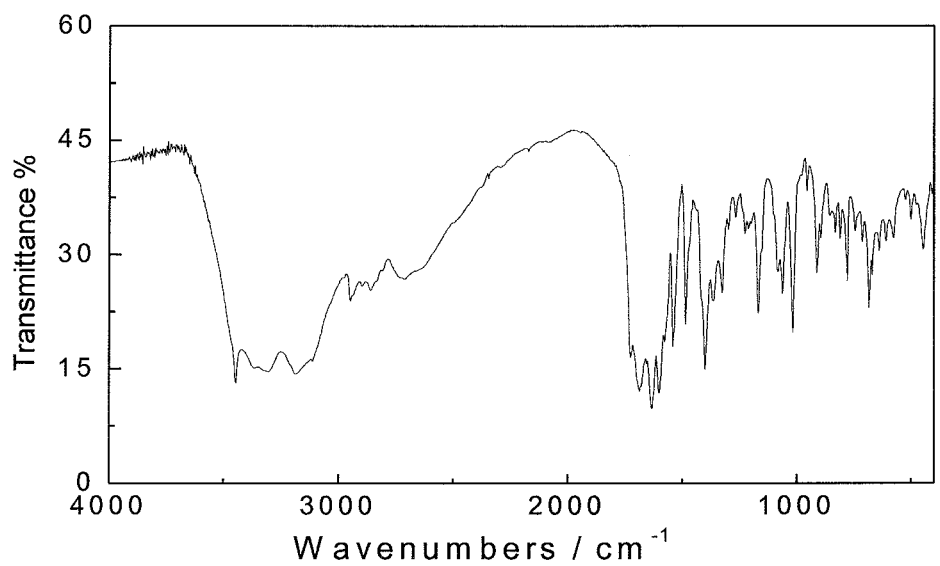
FIG. 3 is Fourier transform infrared spectrogram of the crystalline form of entecavir.

Fourier Transform Infrared (FTIR) Spectrogram:

The range of wave numbers is measured by using the Nicolet NEXUS 670 FT-IR spectrometer with KBr pellet method, and the range of wave numbers is about 400~4000 $cm^{-1}$. FIG. 3 is a Fourier transform infrared spectrogram of the sample. The infrared spectrogram shows that there are groups in the molecular structure of the sample, such as NH, $NH_2$, HN—C=O, C=C, OH.

Figure 4:
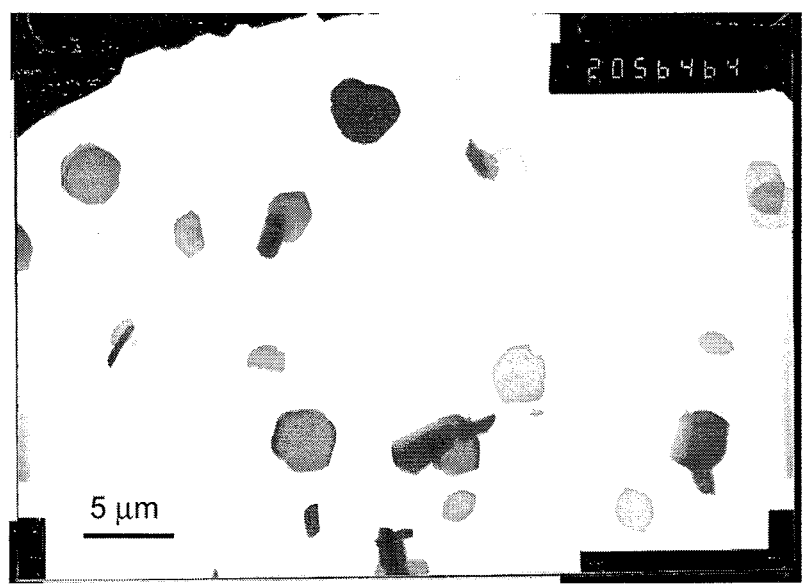
FIG. 4 is spectrogram of transmission electron microscope of the crystalline form of entecavir.

Transmission Electron Microscope:

A few solid samples are dispersed in ethanol under the ultrasonic wave. Then the sample is dropped onto a copper sheet coating a carbon film, and after the evaporating of, the shape and particle size of the crystalline form of entecavir are observed by using a JEM-200 CX transmission electron microscope, please refer to FIG. 4. The accelerating voltage of the transmission electron microscope is about 160 kV. It can be seen from it that the sample is a flaky little crystal, hexagon in shape with 1~5 micron in a particle size.

Solubility:

At a room temperature, the crystalline form of entecavir is insoluble in water, slightly soluble in ethanol, sparingly soluble in N. N-dimethylformamide, and soluble in dimethyl sulfoxide.

Hereinafter, the crystalline form of entecavir of the present invention will be further described by the examples, but it should not be construed as the limitation of the present invention.

Example 1

A crude product of entecavir (10 g) and water (200 g) are added in a reaction bottle, heated to the temperature of 90° C., the above solution is stirred till the solid is completely dissolved, then cooled slowly to the temperature of 50° C., a flaky crystal is separated out of it. After filtration, the crystal is dried for 24 hours in vacuum at the temperature of 50° C. to give the crystalline form of entecavir (7.0 g), that is, [1S-(1α, 3α, 4β)]-2-amino-1,9-dihydro-9-[4-hydroxy-3-hydroxymethyl]-2-methylenecyclopentyl]-6H-purin-6-one.

Example 2

A crude product of entecavir (10 g) and water (400 g) are added in a reaction bottle, heated to the temperature of 50° C., acetone (120 ml, the volume ratio is 30%) is added to the above solution and is stirred till the solid is completely dissolved, then cooled slowly to the temperature of 35° C., a flaky crystal is separated out of it. After filtration, the crystal is dried for 24 hours in vacuum at the temperature of 50° C. to give the crystalline form of entecavir (8.3 g), that is, [1S-(1α, 3α, 4β)]-2-amino-1,9-dihydro-9-[4-hydroxy-3-hydroxymethyl]-2-methylenecyclopentyl]-6H-purin-6-one.

Example 3

A crude product of entecavir (10 g) and water (500 g) are added in a reaction bottle, heated to the temperature of 65° C. ethanol (25 ml, the volume ratio is 5%) is added to the above solution and is stirred till the solid is completely dissolved, then cooled slowly to 15° C., a flaky crystal is separated out of it. After filtration, the crystal is dried for 24 hours in vacuum at the temperature of 50° C. to give the crystalline form of entecavir (9.1 g), that is, [1S-(1α, 3α, 4β)-2-amino-1,9-dihydro-9-[4-hydroxy-3-hydroxymethyl]-2-methylenecyclopentyl]-6H-purin-6-one.

Example 4

A crude product of entecavir (10 g) and water (400 g) are added in a reaction bottle, heated to 80° C. isopropanol (80 ml) and butanone (120 ml) (the volume ratio is 5096) are added to the above solution and are stirred till the solids are completely dissolved, then cooled slowly to the temperature of 10° C., a flaky crystal I is separated out of it. After filtration, the crystal is dried for 24 hours in vacuum at the temperature of 50° C. to give the crystalline form of entecavir (9.4 g), that is, [1S-(1α, 3α, 4β)]-2-amino-1,9-dihydro-9-[4-hydroxy-3-hydroxymethyl]-2-methylenecyclopentyl]-6H-purin-6-one.

Example 5

A crude product of entecavir (10 g) and water (400 g) are added in a reaction bottle, heated to 80° C., methanol (60 ml, the volume ratio is 15%) is added to the above solution and is stirred till the solid is completely dissolved, then cooled slowly to the temperature of 50° C., a flaky crystal is separated out of it. After filtration, the crystal is dried for 24 hours in vacuum at the temperature of 50° C. to give the crystalline form of entecavir (9.5 g), that is, [1S-(1α, 3α, 4β)]-2-amino-1,9-dihydro-9-[4-hydroxy-3-hydroxymethyl]-2-methylenecyclopentyl]-6H-purin-6-one.

Example 6

A crude product of entecavir (10 g) and water (400 g) are added in a reaction bottle, heated to the temperature of 80° C., butanol (80 ml) and butanone (120 ml) (the volume ratio is 50%) are added to the above solution and are stirred till the solids are completely dissolved, then cooled slowly to the temperature of 0° C., a flaky crystal is separated out of it. After filtration, the crystal is dried for 24 hours in vacuum at the temperature of 50° C. to give the crystalline form of entecavir (9.2 g), that is, [1S-(1α, 3α, 4β)]-2-amino-1,9-dihydro-9-[4-hydroxy-3-hydroxymethyl]-2-methylenecyclopentyl]-6H-purin-6-one.

Example 7

And please refer to Table 2, the preparation of tablets of the crystalline form of entecavir is carried by the following procedure.

Process of Preparation

The crystalline form of entecavir, microcrystalline cellulose, lactose, carboxymethyl starch sodium and magnesium stearate are respectively screened by 100 mesh size to reserve.

The crystalline form of entecavir, microcrystalline cellulose and lactose are weighed exactly according to prescription. After mixed thoroughly, starch paste is added to form a soft material. Damp particles are screened by 14 mesh size.

The damp particles are dried for 2 hours at about the temperature of 70° C. to give dry particles, and screened by 14 mesh size to get dry particles. Then carboxymethyl starch sodium and magnesium stearate are added to the dry particles. After mixed thoroughly, the mixture is prepared to be depressed.

The above samples are taken to measure a moisture content of the particles, and the weight of the table and its control range are calculated. Then core tablets are obtained by using a 7.0 mm hollow circle mold.

A coating powder is prepared according to a prescription. The coating powder is added to a purified water under the stirring condition to prepare homogenous suspension containing 20% solid content to reserve.

After removed fine powders and small flashes around the edge, the core tablets are put into a coating pan and heated to the temperature of 45° C.~55° C. then a coating solution is sprayed into the coating pan and dried in hot air at the temperature of 50° C.~60° C. Spouting velocity, air temperature in inlet, and air temperature in outlet are adjusted till the surface of the core tablets is wet but not adhesive. After the core tablets are coated to a suitable coating, the liquid is stopped spraying and the tablets are dried by hot air. Then the film coating tablets are taken out of it, that is, the tablets of entecavir are obtained. We ht increment of the coating is controlled to about 4%.

TABLE 2

| | Names of Raw and Supplemental Materials | Prescription (g) |
|---|---|---|
| Prescription of tcore tablets | Crystalline forms of entecavir, | 0.5 |
| | Microcrystalline cellulose | 95.0 |
| | Lactose | 45.3 |
| | Starch paste | 5.0 (calculating according to starch) |
| | Carboxymethyl starch sodium | 3.0 |
| | Magnesium stearate | 1.2 |
| Prescription of film coating tablets | Hypromellose | 3.6 |
| | Titanium dioxide | 0.78 |
| | Talcum powder | 0.78 |
| | Polyethylene glycol | 0.84 |
| | Purified water | 24.0 |
| Making into | 1000 tablets | |

We claim:

1. A method for preparing a crystalline form of entecavir containing one water of crystallization, the method comprising the steps of:
   dissolving a crude product of entecavir in a polar solvent at approximately 50-90° C. in a ratio of a crude product of entecavir to a polar solvent of 1:20 to 1:60 (mass) to form an entecavir solution, wherein the polar solvent is a solution of water and methanol, or a solution of water and ethanol, or a solution of water and acetone, or a solution of water and butanone, or a solution of water, isopropanol and butanone, or a solution of water, butanol, and butanone;
   cooling the entecavir solution to a temperature of below about 50° C., wherein a crystal separates out of the solution; and
   separating the crystal to obtain the crystalline form of entecavir containing one water of crystallization.

2. The method according to claim 1, wherein the volume ratio of acetone to water, or butanone to water, or ethanol to water, or methanol to water, or isopropanol and butanone to water, or butanol and butanone to water is greater than 0% and less than or equal to 50%.

3. The method for preparing a crystalline form of entecavir containing one water of crystallization according to claim 1, wherein the crystalline form of entecavir has an X-ray powder crystal diffraction pattern within the following scope of 2θ when measured using CuKα radiation,

| 2θ (°) | d (Å) | I % |
|---|---|---|
| 5.282 | 16.7171 | 100.0 |
| 10.573 | 8.3601 | 8.6 |
| 14.876 | 5.9501 | 6.0 |
| 15.560 | 5.6902 | 89.7 |
| 15.895 | 5.5710 | 21.4 |
| 16.643 | 5.3223 | 7.3 |
| 17.304 | 5.1205 | 19.5 |
| 19.741 | 4.4935 | 18.1 |
| 21.236 | 4.1803 | 55.5 |
| 21.658 | 4.0999 | 6.1 |
| 23.681 | 3.7540 | 16.3 |
| 25.040 | 3.5533 | 49.5 |
| 25.619 | 3.4743 | 48.8 |
| 25.844 | 3.4445 | 7.6 |
| 26.338 | 3.3810 | 16.7 |
| 26.637 | 3.3438 | 20.6 |
| 27.201 | 3.2757 | 7.9 |
| 27.655 | 3.2229 | 13.5 |
| 28.143 | 3.1682 | 5.5 |
| 28.440 | 3.1358 | 4.6 |
| 29.686 | 3.0069 | 9.2 |
| 32.085 | 2.7874 | 40.0 |
| 32.466 | 2.7555 | 6.8 |
| 32.939 | 2.7170 | 5.5 |
| 38.862 | 2.3155 | 6.3 |
| 40.443 | 2.2285 | 7.1 | wherein 2θ is the diffraction angle, d is the interplanar spacing of crystal, and I is the relative intensity of a diffraction peak.

4. The method for preparing a crystalline form of entecavir containing one water of crystallization according to claim 1, further comprising formulating a pharmaceutical composition comprising a pharmaceutically acceptable carrier and a therapeutically effective amount of the crystalline form of entecavir containing one water of crystallization.

5. The method for preparing a crystalline form of entecavir containing one water of crystallization according to claim 4, wherein the therapeutically effective amount of the entecavir is from 0.1 mg to 10 mg.

6. The method for preparing a crystalline form of entecavir containing one water of crystallization according to claim 5, wherein the pharmaceutical composition is in a dosage form chosen from tablets, capsules, granules, oral solutions, and injections.

7. The method for preparing a crystalline form of entecavir containing one water of crystallization according to claim 4, further comprising administering the pharmaceutical composition of entecavir for the treatment of hepatitis B viral infection.

8. The method for preparing a crystalline form of entecavir containing one water of crystallization according to claim 1, wherein the polar solvent is a solution of water and methanol, or a solution of water and ethanol, or a solution of water and acetone, or a solution of water, isopropanol and butanone, or a solution of water, butanol, and butanone.

* * * * *